(12) United States Patent
Tong et al.

(10) Patent No.: US 11,547,374 B2
(45) Date of Patent: Jan. 10, 2023

(54) C-ARM X-RAY MACHINE AND SYSTEM, COLLISION MONITORING METHOD AND APPARATUS

(71) Applicant: Siemens Healthcare GmbH, Erlangen (DE)

(72) Inventors: Yu Tong, Shenzhen (CN); Ge Jing, Shenzhen (CN); Jian Qiao Zhang, Shenzhen (CN)

(73) Assignee: Siemens Healthcare GmbH, Erlangen (DE)

(*) Notice: Subject to any disclaimer, the term of this patent is extended or adjusted under 35 U.S.C. 154(b) by 147 days.

(21) Appl. No.: 16/849,298

(22) Filed: Apr. 15, 2020

(65) Prior Publication Data

US 2020/0323498 A1 Oct. 15, 2020

(30) Foreign Application Priority Data

Apr. 15, 2019 (CN) .......................... 201910298344.8

(51) Int. Cl.
*A61B 6/00* (2006.01)
*A61B 6/10* (2006.01)
*A61B 6/04* (2006.01)

(52) U.S. Cl.
CPC ............ *A61B 6/105* (2013.01); *A61B 6/0407* (2013.01); *A61B 6/4441* (2013.01); *A61B 6/5217* (2013.01); *A61B 6/548* (2013.01)

(58) Field of Classification Search
CPC ..................................................... A61B 6/102
See application file for complete search history.

(56) References Cited

U.S. PATENT DOCUMENTS

| 6,272,368 B1 * | 8/2001 | Alexandrescu ........ A61B 6/488 600/407 |
| 2006/0274888 A1 | 12/2006 | Bernhardt et al. |
| 2009/0015669 A1 | 1/2009 | Klingenbeck-Regn |
| 2013/0083894 A1 | 4/2013 | Niebler et al. |
| 2016/0296185 A1 | 10/2016 | Gemmel et al. |

FOREIGN PATENT DOCUMENTS

| CN | 103027699 A | 4/2013 |
| CN | 205434154 U | 8/2016 |
| CN | 106361430 A | 2/2017 |

\* cited by examiner

*Primary Examiner* — Dani Fox
(74) *Attorney, Agent, or Firm* — Banner & Witcoff Ltd.

(57) ABSTRACT

A collision monitoring apparatus can include a camera to acquire a video image of surroundings of at least one target protection component on the C-arm X-ray machine system; an image processor to determine a scene of the surroundings of the at least one target protection component according to the video image; and a controller to control a C-arm X-ray machine system to stop moving or slow down when it is determined that a possible collision exists according to the scene of the surroundings of the at least one target protection component. Advantageously the apparatus effectively prevents patients, operators, patient examination beds and other obstacles from suffering a serious collision with the C-arm itself.

16 Claims, 3 Drawing Sheets

C-ARM X-RAY MACHINE AND SYSTEM, COLLISION MONITORING METHOD AND APPARATUS

CROSS REFERENCE TO RELATED APPLICATIONS

This patent application claims priority to Chinese Patent Application No. 201910298344.8, filed Apr. 15, 2019, which is incorporated herein by reference in its entirety.

BACKGROUND

Field

The present disclosure relates to the field of X-ray imaging systems, in particular to a collision monitoring method and a collision monitoring apparatus for a C-arm X-ray machine system, and a corresponding C-arm X-ray machine and C-arm X-ray machine system.

Related Art

C-arm X-ray machine systems, such as angiography machine systems, have found extensive use in the medical field as medical instruments. In a C-arm X-ray machine system, an X-ray source and an X-ray receiver (e.g. a flat-panel detector) are mounted opposite one another on a C-arm, such that X-rays produced by the X-ray source are incident on the X-ray receiver and detected by the latter. When an X-ray examination is carried out, an object under examination such as a human body is placed between the X-ray source and X-ray receiver by a patient examination bed; by changing the position and angle of the C-arm and/or controlling a patient examination platform, the position of the object under examination is changed, and the positions of the X-ray source and the X-ray receiver relative to the object under examination are changed, such that the X-ray machine can perform an X-ray examination of the object under examination from multiple different positions and angles.

Figure 1:
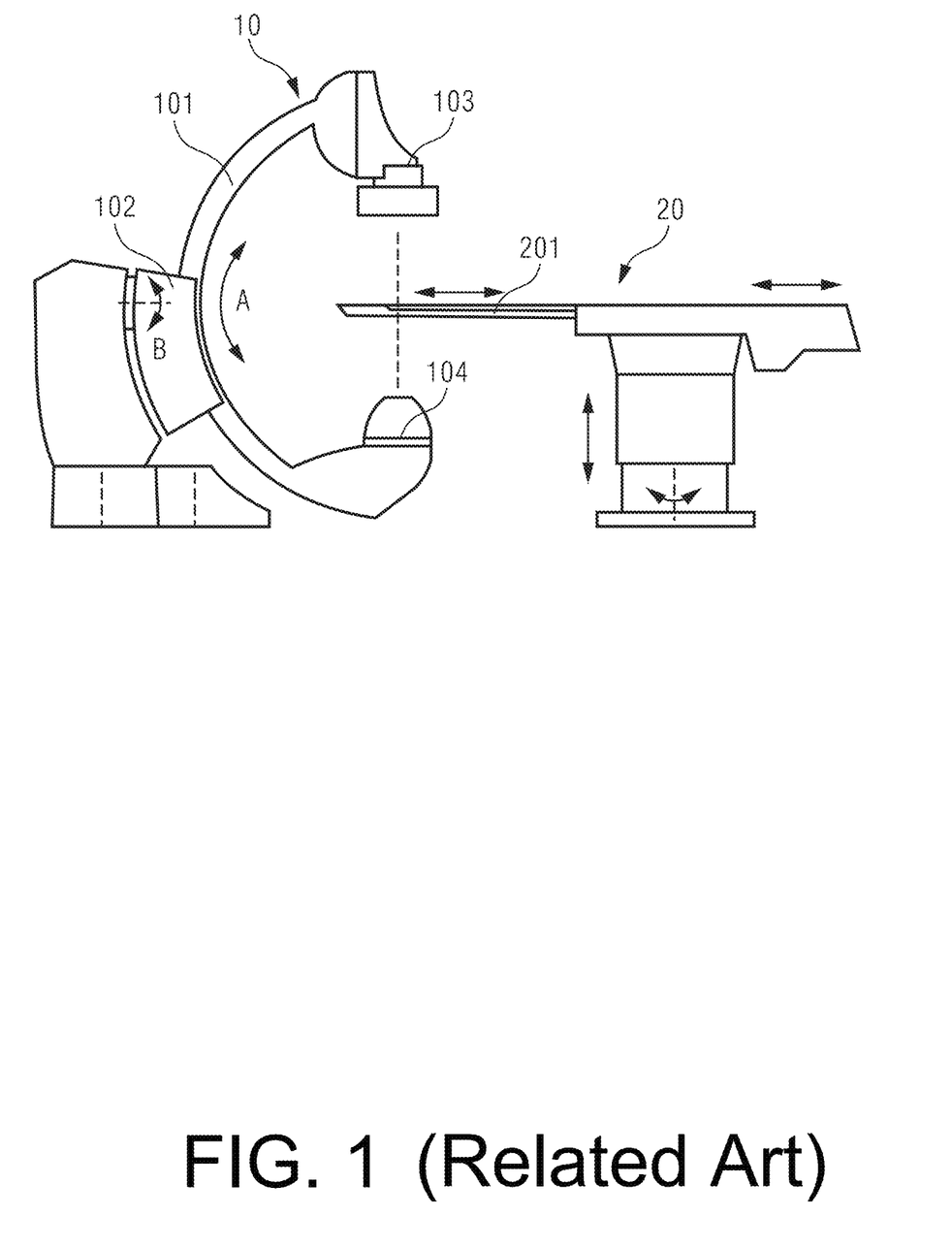
FIG. 1 shows a conventional C-arm X-ray machine system.

For this purpose, a C-arm generally has multiple degrees of freedom. FIG. 1 shows a structural schematic drawing of an existing C-arm X-ray machine system; taking the C-arm X-ray machine system shown in FIG. 1 as an example, the C-arm X-ray machine system comprises: a C-arm X-ray machine 10 and a patient examination bed 20. A C-arm 101 of the C-arm X-ray machine is itself mounted in such a way as to have two degrees of freedom. First of all, the C-arm 101 has a guide rail disposed along its own shape, the guide rail of the C-arm 101 being slidably mounted on a supporting member 102 in order to be able to move relative to the supporting member 102, i.e. the C-arm 101 can perform orbital movement A as shown in FIG. 1; secondly, the supporting member 102 can drive the C-arm 101 to rotate around an axis thereof, i.e. the C-arm 101 can also perform rotational (angular) movement B as shown in FIG. 1. In addition, the C-arm 101 shown in FIG. 1 also has a third degree of freedom of horizontal movement along the floor, etc. In addition, the patient examination bed might also have multiple degrees of freedom. Thus, a collision might sometimes occur between the C-arm and a patient, medical personnel, the patient examination bed or another obstacle, etc. due to personnel being careless with movement of the C-arm or patient examination platform or due to the C-arm or patient examination platform being operated erroneously; this might not only cause injury to personnel, but might also cause damage to the C-arm or obstacle. Thus, in order to make the C-arm X-ray machine safer for patients and medical personnel and reduce the possibility of damage to the C-arm itself, the C-arm X-ray machine must have a collision prevention design.

Thus, those skilled in the art have for a long time been making efforts to seek out different solutions for enabling collision monitoring of C-arm X-ray machines.

Chinese Patent application publication no. CN106361430A has disclosed a medical apparatus, comprising: a moving part; at least one sensor, disposed on the moving part and forming a field in a movement direction of the moving part, the field having a boundary, wherein when an object is located at multiple points between the boundary and the sensor, the sensor transmits a signal related to the distance between the point and the sensor; and a speed limiter, which limits a movement speed of the moving part according to the signal. The medical apparatus can detect the entry of the object into the field formed by the sensor and correspondingly adjust the speed of the moving part, in order to avoid a collision.

Chinese utility model no. CN205434154U provides a patient bed collision prevention apparatus and a patient bed, comprising: an image acquisition apparatus, for acquiring a real-time image in a collision monitoring region close to the patient bed; and a central processor, which is disposed on the patient bed, and controls movement of the patient bed according to the real-time image captured by the image acquisition apparatus. According to that utility model, it is possible to monitor in real time obstacles which appear in the vicinity of the patient bed, and stop the movement of the patient bed when an obstacle appears, thereby ensuring the safety of the patient bed.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

Aspects of the present disclosure include a collision monitoring method and apparatus for a C-arm X-ray machine system, a C-arm X-ray machine, and a C-arm X-ray machine system.

Aspects of the present disclosure advantageously reduce and/or prevent patients, operators, patient examination beds and other obstacles from suffering a serious collision with the C-arm itself.

A collision monitoring apparatus for a C-arm X-ray machine system proposed in an embodiment of the present disclosure comprises: a camera, for acquiring a video image of surroundings of at least one target protection component on the C-arm X-ray machine system; an image processor, for determining a scene of the surroundings of the at least one target protection component according to the video image; and a controller, for controlling the C-arm X-ray machine system to stop moving or slow down when it is determined that a possible collision exists according to the scene of the surroundings of the at least one target protection component.

In one embodiment, the C-arm X-ray machine system comprises a C-arm X-ray machine and a patient examination platform; the at least one target protection component comprises: at least two target protection components, specifically a bed board of the patient examination platform, and an X-ray source and/or an X-ray receiver and/or a C-arm; the camera comprises at least three of the following cameras: cameras located directly above, directly in front of, and at two sides of the C-arm X-ray machine, and cameras located at two sides of the patient examination platform, for acquiring video images of the surroundings of the at least two target protection components from different directions respectively, to obtain video streams of at least three channels; the image processor comprises: an image extractor, for subjecting the video streams of the at least three channels from the at least three cameras to synchronization, and extracting corresponding images of the at least three channels according to a set frequency; and an image identifier, for subjecting the corresponding images of the at least three channels to target protection component identification and scene analysis, to obtain a relative position relationship of the at least two target protection components; the controller determines whether a possible collision exists according to the relative position relationship of the at least two target protection components.

In one embodiment, the image processor further comprises an image preprocessor, for subjecting the images of the at least three channels extracted by the image extractor to target object identification, the target object being the C-arm X-ray machine system; and removing an object other than the identified target object from the images, and supplying the images from which the object has been removed to a trained image completion model, and obtaining completed images outputted by the image completion model; the image identifier executes the operation of performing target protection component identification and scene analysis on the basis of the completed corresponding images of the at least three channels.

In one embodiment, the C-arm X-ray machine system comprises: a position detector for determining a current movement position of a C-arm; the at least one target protection component comprises: an X-ray source or an X-ray receiver; the camera comprises: at least one camera mounted at the X-ray source side or at least one camera mounted at the X-ray receiver side; the image processor is configured to determine whether an obstacle appears in a target region according to the video image from the at least one camera, and when an obstacle appears in the target region, performing positioning of the obstacle to obtain a current position of the obstacle; the controller is further configured to determine a current movement direction of the C-arm, and when the current movement direction is toward the current position of the obstacle, determining a distance value between the target protection component and the obstacle according to the current movement position of the C-arm and the current position of the obstacle, and determining whether a possible collision exists according to the distance value.

In one embodiment, the movement position comprises: a rotational movement position, an orbital movement position or a horizontal movement position.

In one embodiment, the movement direction comprises: any one of a rotational movement forward direction, a rotational movement reverse direction, an orbital movement forward direction, an orbital movement reverse direction, a horizontal movement forward direction and a horizontal movement reverse direction.

A C-arm X-ray machine system proposed in an embodiment of the present disclosure comprises the collision monitoring apparatus in any one of the above embodiments.

A C-arm X-ray machine proposed in an embodiment of the present disclosure comprises the collision monitoring apparatus in any one of the above embodiments.

A collision monitoring method for a C-arm X-ray machine system proposed in an embodiment of the present disclosure comprises: acquiring a video image of surroundings of at least one target protection component on the C-arm X-ray machine system; determining a scene of the surroundings of the at least one target protection component according to the video image; and determining whether a possible collision exists according to the scene of the surroundings of the at least one target protection component, and when a possible collision exists, controlling the C-arm X-ray machine system to stop moving or slow down.

In one embodiment, the at least one target protection component comprises: at least two target protection components, specifically a bed board of a patient examination platform, and an X-ray source and/or an X-ray receiver and/or a C-arm; the step of acquiring a video image of surroundings of at least one target protection component on the C-arm X-ray machine system comprises: acquiring video images of the surroundings of the at least two target protection components from at least three directions respectively, to obtain video streams of at least three channels; the at least three directions comprising at least three of the following directions: directly above, directly in front of, and at two sides of the C-arm X-ray machine, and at two sides of the patient examination platform; the step of determining a scene of the surroundings of the at least one target protection component according to the video image comprises: subjecting the video streams of the at least three channels to synchronization, and extracting corresponding images of the at least three channels according to a set frequency; and subjecting the corresponding images of the at least three channels to target protection component identification and scene analysis, to obtain a relative position relationship of the at least two target protection components; the step of determining whether a possible collision exists according to the scene of the surroundings of the at least one target protection component comprises: determining whether a possible collision exists according to the relative position relationship of the at least two target protection components.

In one embodiment, the method further comprises: subjecting the images of the at least three channels to target object identification, the target object being the C-arm X-ray machine system; removing an object other than the identified target object from the current image; supplying the images from which the object has been removed to a trained image completion model, and obtaining completed images outputted by the image completion model; the step of subjecting the corresponding images of the at least three channels to target protection component identification and scene analysis consists of: performing target protection component identification and scene analysis on the basis of the completed corresponding images of the at least three channels.

In one embodiment, the at least one target protection component comprises: a collimator of the X-ray source or an image enhancer at the X-ray receiver side; the step of acquiring a video image of surroundings of at least one target protection component on the C-arm X-ray machine system comprises: acquiring a video image of the surroundings of the collimator from the X-ray source side or acquiring a video image of the surroundings of the image enhancer from the X-ray receiver side; the step of determining a scene of the surroundings of the at least one target protection component according to the video image comprises: determining whether an obstacle appears in a target region according to the video image, and when an obstacle appears in the target region, performing positioning of the obstacle to obtain a current position of the obstacle; the method further comprising: determining a current movement position and a current movement direction of a C-arm; the step of determining whether a possible collision exists according to the scene of the surroundings of the at least one target protection component comprises: determining whether the current movement direction is toward the current position of the obstacle, and if the current movement direction is toward the current position of the obstacle, determining a distance value between the target protection component and the obstacle according to the current movement position of the C-arm and the current position of the obstacle, and determining whether a possible collision exists according to the distance value.

It can be seen from the solution above that in embodiments of the present disclosure, according to at least one target protection component on the C-arm X-ray machine system that is determined in advance, the camera is disposed to acquire a video image of the surroundings of the at least one target protection component; a scene of the surroundings of the at least one target protection component is then determined by the image processor according to the video image; a determination is then made as to whether a possible collision exists by the controller according to the scene of the surroundings of the at least one target protection component, and when a possible collision exists, the C-arm X-ray machine system is controlled to stop moving or slow down. A collision monitoring solution based on visual analysis is thereby realized, which can not only effectively prevent patients, operators, patient examination beds and other obstacles from suffering a serious collision with the C-arm itself, but also makes full use of image processing technology and intelligent computer technology which are developing rapidly at the present time.

In addition, a solution is proposed in which video images of the surroundings of at least two target protection components, specifically the patient examination platform and the X-ray source and/or X-ray receiver and/or C-arm are acquired from different directions, and a position relationship between the X-ray source and/or X-ray receiver and the patient examination platform is acquired on the basis of visual analysis to determine whether the possibility of collision exists, and it is thereby possible to avoid a collision between the X-ray source and/or X-ray receiver on the C-arm and the patient examination platform.

Furthermore, in cases where obscuring objects are present in the video images acquired, a target object is identified using image identification technology, objects other than the target object, i.e. possible obscuring objects, are then removed, and the images from which the possible obscuring objects have been removed are then completed using image completion technology, thereby obtaining video images without any obscurement, avoiding inaccuracy in collision monitoring due to obscurement. Image completion is performed using a trained image completion model, and can thereby be accomplished rapidly.

In addition, a solution is proposed in which a video image of the surroundings of a collimator or image enhancer is acquired, a determination is made as to whether an obstacle appears in a target region and a current position of the obstacle is determined on the basis of image identification and positioning technology, then a current movement position and a current movement direction of the C-arm are acquired, and when the current movement direction is toward the current position of the obstacle, a distance value between the target protection component and the obstacle is determined according to the current movement position of the C-arm and the current position of the obstacle, and a determination is made as to whether a possible collision exists according to the distance value. It is thereby possible to avoid unnecessary collision prevention operations when the distance is small but the movement direction is away from or parallel to the obstacle, further ensuring the accuracy of collision monitoring.

In an embodiment of the present disclosure, in order to perform collision monitoring of a C-arm X-ray machine system, a collision monitoring solution based on visual analysis is proposed. According to at least one target protection component on the C-arm X-ray machine system that has been determined in advance, a camera is disposed to acquire a video image of the surroundings of the at least one target protection component; in a particular implementation, the camera may comprise one or more cameras. A scene of the surroundings of the at least one target protection component is then determined by an image processor according to the video image; in a particular implementation, the image processor may comprise different implementation structures according to different actual demands. A determination is then made as to whether a possible collision exists by a controller according to the scene of the surroundings of the at least one target protection component, and when a possible collision exists, the C-arm X-ray machine system is controlled to stop moving or slow down.

In order to clarify the object, technical solution and advantages of the present disclosure, the present disclosure is explained in further detail below by way of embodiments.

Figure 2:
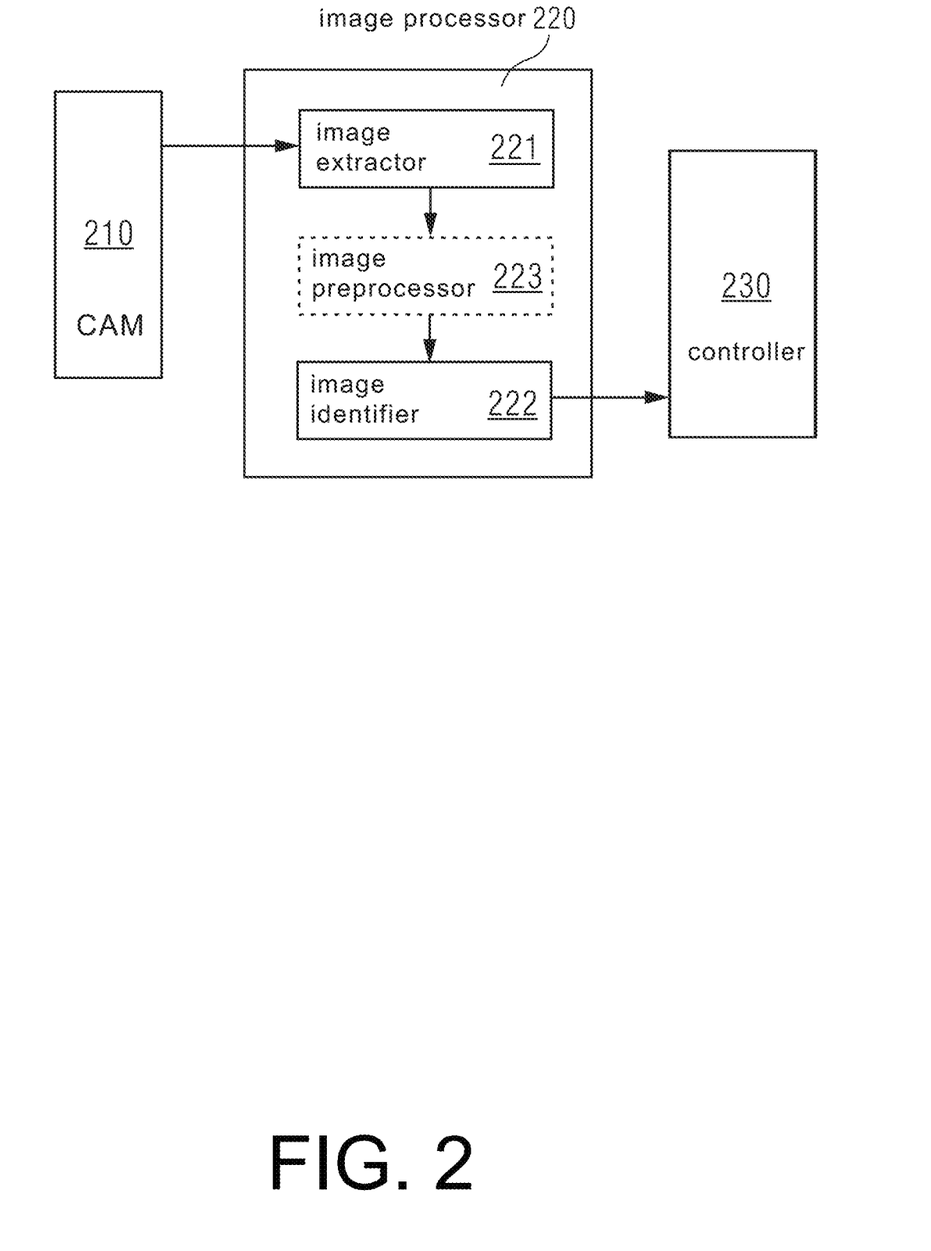
FIG. 2 is a structural schematic diagram of a collision monitoring apparatus for a C-arm X-ray machine system in an embodiment of the present disclosure.

FIG. 2 is a structural schematic diagram of a collision monitoring apparatus for a C-arm X-ray machine system in an embodiment of the present disclosure. As shown by the solid-line part in FIG. 1, the collision monitoring apparatus for the C-arm X-ray machine system may comprise: a camera 210, an image processor 220 and a controller 230.

The camera 210 is configured to acquire a video image of the surroundings of at least one target protection component on the C-arm X-ray machine system.

In this embodiment, the at least one target protection component may comprise at least two target protection components, specifically a bed board 201 of a patient examination platform 20 in the C-arm X-ray machine system as shown in FIG. 1, and an X-ray source 104 and/or an X-ray receiver 103 and/or a C-arm 101, i.e. "at least one of the X-ray source 104, X-ray receiver 103 and C-arm 101" plus the "bed board 201". For example, two target protection components, namely the X-ray source 104 and the bed board 201 of the patient examination platform 20, are included; or two target protection components, namely the X-ray receiver 103 and the bed board 201 of the patient examination platform 20, are included; or three target protection components, namely the X-ray source 104, the X-ray receiver 103 and the bed board 201 of the patient examination platform 20, are included; or two target protection components, namely the C-arm 101 and the bed board 201 of the patient examination platform 20, are included; or three target protection components, namely the X-ray source 104, the C-arm 101 and the bed board 201 of the patient examination platform 20, are included; or three target protection components, namely the X-ray receiver 103, the C-arm 101 and the bed board 201 of the patient examination platform 20, are included; or four target protection components, namely the X-ray source 104, the X-ray receiver 103, the C-arm 101 and the bed board 201 of the patient examination platform 20, are included. Correspondingly, the camera 210 may comprise two cameras (not shown in the figures) located directly above the C-arm X-ray machine 10 and directly in front of the C-arm X-ray machine (i.e. the direction in which the C-arm X-ray machine 10 directly faces the bed board 201 of the examination platform 20), and one or two cameras (not shown in the figures) located at one or two sides of the patient examination platform 20 (i.e. the directions in which the C-arm X-ray machine 10 obliquely faces the bed board 201 of the examination platform 20, or may further comprise one or two cameras located at one or two sides of the C-arm X-ray machine 10. Thus, video images acquired by the cameras in at least three directions can form video streams of at least three channels. In this embodiment, the video image of the surroundings of the target protection component includes the target protection component itself.

The image processor 220 is configured to determine a scene of the surroundings of the at least one target protection component according to the video image.

In this embodiment, for the video streams of the at least three channels, the image processor 220 may first of all subject them to synchronization, and extract corresponding images of the at least three channels according to a set frequency, and then subject the corresponding images of the at least three channels to target protection component identification and scene analysis, to obtain a relative position relationship of the at least two target protection components. The specific process of subjecting the corresponding images of the at least three channels to target protection component identification and scene analysis may take more than one form. For example, it is possible to identify the corresponding target protection component in each image on the basis of a contour or characteristic point of the target protection component, acquire a pixel point position of the corresponding target protection component in the image, calculate by conversion a spatial position of the target protection component in a real scene according to the pixel point position of the target protection component in the image, and integrate the spatial positions of the target protection components determined according to the corresponding images of the at least three channels, to obtain the relative position relationship of the at least two target protection components.

In particular implementation, in one embodiment, the image processor 220 may comprise, as shown in FIG. 2: an image extractor 221 and an image identifier 222. The image extractor 221 is configured to subject the video streams of the at least three channels to synchronization, and extract corresponding images of the at least three channels according to a set frequency. The image identifier 222 is configured to subject the corresponding images of the at least three channels to target protection component identification and scene analysis, to obtain a relative position relationship of the at least two target protection components.

In addition, taking into account the fact that in some application scenarios, for example in interventional surgery scenarios, situations will arise where equipment of the C-arm X-ray machine system is obscured by doctors, nurses, surgical sheets and surgical tools, etc., in order to avoid possible effects on the image processing result in such scenarios, consideration is given to the action of removing obscuring objects from the captured image, and then completing the equipment parts corresponding to the obscuring objects on the basis of image completion technology. In particular implementation, taking into account the fact that in medical scenarios, equipment of the C-arm X-ray machine system is generally white, whereas doctors' and nurses' surgical gowns, surgical sheets and surgical tools are silver or green, it is possible to identify an equipment contour of the C-arm X-ray machine system on the basis of color, then take objects other than the C-arm X-ray machine system to be possible obscuring objects, remove images of regions corresponding to the possible obscuring objects from the captured image, and then subject the image from which obscuring object regions have been removed to image completion. For example, in this embodiment, the image processor 220 may further subject the extracted images of the at least three channels to target object identification on the basis of an equipment contour or characteristic point of the C-arm X-ray machine system, the target object being the C-arm X-ray machine system; and remove objects other than the identified target object from the images, and supply the images from which the objects have been removed to a trained image completion model, and obtain completed images outputted by the image completion model, thereby completely restoring an actual machine movement posture. The operation of performing target protection component identification and scene analysis is then executed on the basis of the completed corresponding images of the at least three channels. Correspondingly, in another embodiment, the image processor 220 may further comprise, as shown by the dotted-line part in FIG. 1, an image preprocessor 223, configured to subject the images of the at least three channels that have been extracted by the image extractor 221 to target object identification on the basis of an equipment contour or characteristic point, etc. of the C-arm X-ray machine system, wherein the target object is the C-arm X-ray machine system; and when identifying the target object in the images, removing objects other than the target object, i.e. possible obscuring objects, from the current image, and supplying the images from which the possible obscuring objects have been removed to a trained image completion model, and obtaining completed images outputted by the image completion model. Correspondingly, the image identifier 222 executes the operation of performing target protection component identification and scene analysis on the basis of the completed corresponding images of the at least three channels.

The controller 230 is configured to control the C-arm X-ray machine system to stop moving or slow down when it is determined that a possible collision exists according to the scene of the surroundings of the at least one target protection component. When the C-arm is controlled to stop moving, a collision zone escape strategy may further be initiated, e.g. a motor driver currently driving the C-arm to move is controlled to move in an opposite direction, e.g. move by a minute amount in the opposite direction.

In an embodiment of the present disclosure, the controller 230 may determine whether a possible collision exists according to the relative position relationship of the at least two target protection components. For example, a distance threshold between the X-ray source and the patient examination platform, and/or between the X-ray receiver and the patient examination platform, may be set in advance, and when the distance between the X-ray source and the patient examination platform or the distance between the X-ray receiver and the patient examination platform reaches the corresponding distance threshold, it is determined that a possible collision exists. Here, the distance threshold may also have multiple levels, e.g. a reminder level threshold and a warning level threshold, etc., and correspondingly, different types of control may be executed according to different situations; for example, when the reminder level threshold is reached, the patient examination platform or C-arm in the C-arm X-ray machine system may be controlled to slow down. When the warning level threshold is reached, the patient examination platform or C-arm in the C-arm X-ray machine system may be controlled to stop moving. In an exemplary embodiment, the controller 230 includes processor circuitry that is configured to perform one or more operations and/or functions of the controller 230.

Figure 3:
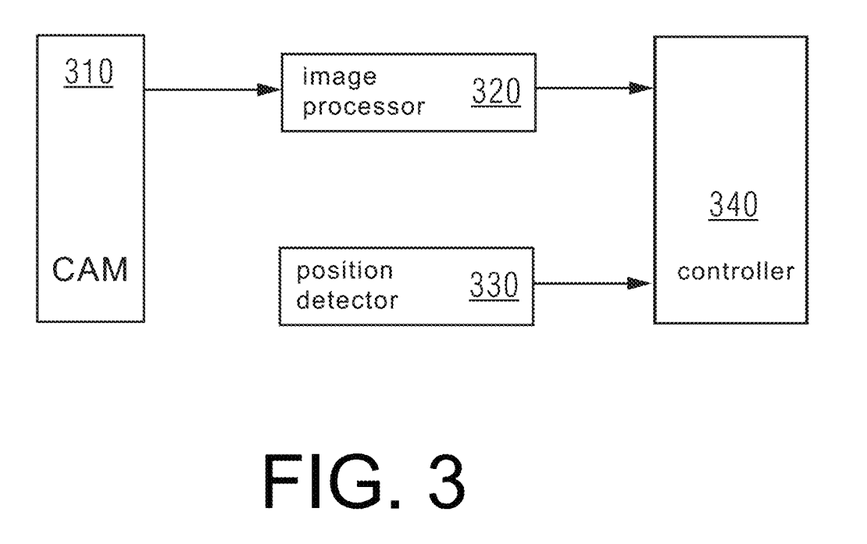
FIG. 3 is a structural schematic diagram of a collision monitoring apparatus for a C-arm X-ray machine system in an embodiment of the present disclosure.

FIG. 3 is a structural schematic diagram of a collision monitoring apparatus for a C-arm X-ray machine system in another embodiment of the present disclosure. As shown in FIG. 3, the collision monitoring apparatus for the C-arm X-ray machine system may comprise: a camera 310, an image processor 320, a position detector 330 and a controller 340.

The camera 310 is configured to acquire a video image of the surroundings of at least one target protection component on the C-arm X-ray machine system.

In this embodiment, the at least one target protection component may comprise a collimator at the X-ray source 104 side, or an image enhancer at the X-ray receiver 103 side, in the C-arm X-ray machine system as shown in FIG. 1. Correspondingly, the camera 310 may comprise at least one camera mounted at the X-ray source 104 side, for acquiring a video image of the surroundings of the collimator; or comprise at least one camera mounted at the X-ray receiver 103 side, for acquiring a video image of the surroundings of the image enhancer. In this embodiment, the video image of the surroundings of the target protection component may include the target protection component itself, or may not include the target protection component itself.

The image processor 320 is configured to determine a scene of the surroundings of the at least one target protection component according to the video image.

In this embodiment, the image processor 320 may, according to the video image of the surroundings of the collimator or image enhancer from the at least one camera, determine whether an obstacle appears in a set target region in the surroundings of the collimator or image enhancer, and when an obstacle appears in the target region, perform positioning of the obstacle to obtain a current position of the obstacle. Positioning of the obstacle may be performed using image processing technology, e.g. a determination may be made according to factors such as camera mounting position, angle and focal length and a region size of the obstacle in the image.

The position detector 330 is configured to determine a current movement position of the C-arm.

In this embodiment, the position detector 330 may comprise a potentiometer or encoder, and/or a position sensor, etc. It may be a component already present on the C-arm X-ray machine, or a component that is newly added in this embodiment.

The controller 340 is configured to control the C-arm X-ray machine system to stop moving or slow down when it is determined that a possible collision exists according to the scene of the surroundings of the at least one target protection component. When the C-arm is controlled to stop moving, a collision zone escape strategy may further be initiated, e.g. a motor driver currently driving the C-arm to move is controlled to move in an opposite direction, e.g. move by a minute amount in the opposite direction.

In this embodiment, the controller 340 may be further configured to determine a current movement direction of the C-arm, and when the current movement direction is toward the current position of the obstacle, determine a distance value between the target protection component and the obstacle according to the current movement position of the C-arm and the current position of the obstacle, and determine whether a possible collision exists according to the distance value. For example, a distance threshold between the two may be set in advance, and when the distance value between the two reaches the corresponding distance threshold, it is determined that a possible collision exists. Here, the distance threshold may also have multiple levels, e.g. a reminder level threshold and a warning level threshold, etc., and correspondingly, different types of control may be executed according to different situations; for example, when the reminder level threshold is reached, the C-arm in the C-arm X-ray machine system may be controlled to slow down. When the warning level threshold is reached, the C-arm in the C-arm X-ray machine system may be controlled to stop moving or move in the opposite direction. In an exemplary embodiment, the controller 340 includes processor circuitry that is configured to perform one or more operations and/or functions of the controller 340.

In this embodiment, the movement position may comprise: a rotational movement position, an orbital movement position and a horizontal movement position. Correspondingly, the movement direction may comprise: any one of a rotational movement forward direction (i.e. forward rotation direction of rotational movement), a rotational movement reverse direction (reverse rotation direction of rotational movement), an orbital movement forward direction (i.e. forward rotation direction of orbital movement), an orbital movement reverse direction (i.e. reverse rotation direction of orbital movement), a horizontal movement forward direction (i.e. set forward direction of horizontal movement) and a horizontal movement reverse direction (i.e. set reverse direction of horizontal movement).

The C-arm X-ray machine system provided in an embodiment of the present disclosure may comprise the collision monitoring apparatus in any one of the above embodiments. The C-arm X-ray machine provided in an embodiment of the present disclosure may comprise the collision monitoring apparatus in any one of the above embodiments shown in FIG. 3.

The C-arm X-ray machine system collision monitoring apparatus and C-arm X-ray machine system in embodiments of the present disclosure have been described in detail above; a collision monitoring method for a C-arm X-ray machine system in an embodiment of the present disclosure is described in detail below. The collision monitoring method for a C-arm X-ray machine system in an embodiment of the present disclosure may be realized on the collision monitoring apparatus for a C-arm X-ray machine system in an embodiment of the present disclosure. For details not disclosed in method embodiments of the present disclosure, the corresponding descriptions in apparatus embodiments of the present disclosure may be referred to; such details are not repeated one by one in method embodiments of the present disclosure.

Figure 4:
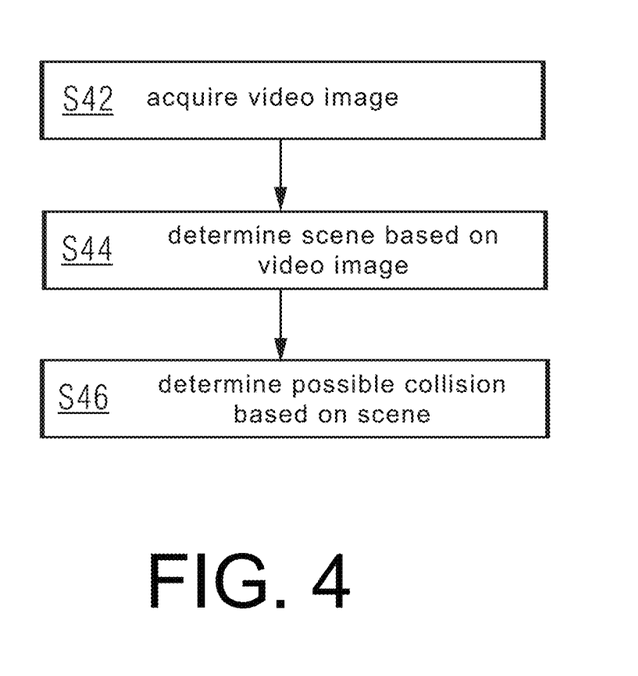
FIG. 4 is a demonstrative flow chart of the collision monitoring method for a C-arm X-ray machine system in an embodiment of the present disclosure.

FIG. 4 is a demonstrative flow chart of the collision monitoring method for a C-arm X-ray machine system in an embodiment of the present disclosure. As FIG. 4 shows, the method may comprise the following steps:

Step S42, acquiring a video image of the surroundings of at least one target protection component on the C-arm X-ray machine system.

In particular implementation, step S42 may be implemented in more than one way. Two examples are given below:

Example 1: When the at least one target protection component comprises at least two target protection components, specifically the bed board 201 of the patient examination platform 20, and the X-ray source 104 and/or X-ray receiver 103 and/or C-arm 101, step S42 may comprise acquiring video images of the surroundings of the at least two target protection components from at least three directions, specifically directly above, directly in front of, and at two sides of the C-arm X-ray machine, and at two sides of the patient examination platform respectively, to obtain video streams of at least three channels.

Example 2: When the at least one target protection component comprises a collimator of the X-ray source or an image enhancer at the X-ray receiver side, step S42 may comprise acquiring a video image of the surroundings of the collimator from the X-ray source side or acquiring a video image of the surroundings of the image enhancer from the X-ray receiver side.

Step S44, determining a scene of the surroundings of the at least one target protection component according to the video image.

In particular implementation, step S44 may be implemented in more than one way.

For example, based on example 1 above, step S44 may comprise subjecting the video streams of the at least three channels to synchronization, and extracting corresponding images of the at least three channels according to a set frequency; and subjecting the corresponding images of the at least three channels to target protection component identification and scene analysis, to obtain a relative position relationship of the at least two target protection components. Furthermore, it is also possible to subject the images of the at least three channels to target object identification on the basis of an equipment contour or characteristic point, etc. of the C-arm X-ray machine system, the target object being the C-arm X-ray machine system; and when a target object has been identified in the images, objects other than the target object, i.e. possible obscuring objects, are removed from the current image; the images from which the possible obscuring objects have been removed are supplied to a trained image completion model, and completed images outputted by the image completion model are obtained; target protection component identification and scene analysis are then performed on the basis of the completed corresponding images of the at least three channels.

As another example, based on example 2 above, step S44 may comprise determining whether an obstacle appears in a set target region in the surroundings of the collimator or image enhancer, according to the video image of the surroundings of the collimator or image enhancer, and when an obstacle appears in the target region, performing positioning of the obstacle to obtain a current position of the obstacle.

Step S46, determining whether a possible collision exists according to the scene of the surroundings of the at least one target protection component, and when a possible collision exists, controlling the C-arm X-ray machine system to stop moving or slow down.

In a particular implementation, step S46 may be implemented in more than one way.

For example, based on example 1 above, step S46 may comprise determining whether a possible collision exists according to the relative position relationship of the at least two target protection components.

As another example, based on example 2 above, the method may further comprise determining a current movement position and a current movement direction of the C-arm; step S46 may comprise determining whether the current movement direction is toward the current position of the obstacle, and if the current movement direction is toward the current position of the obstacle, determining a distance value between the target protection component and the obstacle according to the current movement position of the C-arm and the current position of the obstacle, and determining whether a possible collision exists according to the distance value.

The movement position may comprise: a rotational movement position, an orbital movement position and a horizontal movement position. The movement direction may comprise: any one of a rotational movement forward direction, a rotational movement reverse direction, an orbital movement forward direction, an orbital movement reverse direction, a horizontal movement forward direction and a horizontal movement reverse direction.

It can be seen from the solution above that in embodiments of the present disclosure, according to at least one target protection component on the C-arm X-ray machine system that is determined in advance, the camera is disposed to acquire a video image of the surroundings of the at least one target protection component; a scene of the surroundings of the at least one target protection component is then determined by the image processor according to the video image; a determination is then made as to whether a possible collision exists by the controller according to the scene of the surroundings of the at least one target protection component, and when a possible collision exists, the C-arm X-ray machine system is controlled to stop moving or slow down or move in the opposite direction. A collision monitoring solution based on visual analysis is thereby realized, which can not only effectively prevent patients, operators, patient examination beds and other obstacles from suffering a serious collision with the C-arm itself, but also makes full use of image processing technology and intelligent computer technology which are developing rapidly at the present time.

In addition, a solution is proposed in which video images of the surroundings of at least two target protection components, specifically the patient examination platform and the X-ray source and/or X-ray receiver are acquired from different directions, and a position relationship between the X-ray source and/or X-ray receiver and the patient examination platform is acquired on the basis of visual analysis to determine whether the possibility of collision exists, and it is thereby possible to avoid a collision between the X-ray source and/or X-ray receiver on the C-arm and the patient examination platform.

Furthermore, in cases where obscuring objects are present in the video images acquired, a target object is identified using image identification technology, the target object being the C-arm X-ray machine system; objects other than the target object, i.e. possible obscuring objects, are then removed, and the images from which the possible obscuring objects have been removed are then completed using image completion technology, thereby obtaining video images without any obscurement, avoiding inaccuracy in collision monitoring due to obscurement. Image completion is performed using a trained image completion model, and can thereby be accomplished rapidly.

In addition, a solution is proposed in which a video image of the surroundings of a collimator or image enhancer is acquired, a determination is made as to whether an obstacle appears in a target region and a current position of the obstacle is determined on the basis of image identification and positioning technology, then a current movement position and a current movement direction of the C-arm are acquired, and when the current movement direction is toward the current position of the obstacle, a distance value between the target protection component and the obstacle is determined according to the current movement position of the C-arm and the current position of the obstacle, and a determination is made as to whether a possible collision exists according to the distance value. It is thereby possible to avoid unnecessary collision prevention operations when the distance is small but the movement direction is away from or parallel to the obstacle, further ensuring the accuracy of collision monitoring.

The embodiments above are merely preferred embodiments of the present disclosure, which are not intended to limit it. Any amendments, equivalent substitutions or improvements etc. made within the spirit and principles of the present disclosure shall be included in the scope of protection thereof.

Any connection or coupling between functional blocks, devices, components of physical or functional units shown in the drawings and described hereinafter may be implemented by an indirect connection or coupling. A coupling between components may be established over a wired or wireless connection. Functional blocks may be implemented in hardware, software, firmware, or a combination thereof.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

REFERENCE LIST

10 C-arm X-ray machine
101 C-arm
102 supporting member
103 X-ray receiver
104 X-ray source
20 patient examination platform
201 bed board
210, 310 camera 220, 320 image processor
221 image extractor
222 image identifier
223 image preprocessor
230, 340 controller
330 position detector
S42, S44, S46 operations

The invention claimed is:

1. A collision monitoring apparatus for a C-arm X-ray machine system, comprising:
   a camera configured to acquire a video image of surroundings of at least one target protection component on the C-arm X-ray machine system to obtain video streams of at least three channels;
   an image processor configured to determine a scene of the surrounding of the at least one target protection component based on the video image, the image processor including:
      an image extractor configured to subject the video streams of the at least three channels from the at least three cameras to synchronization, and to extract corresponding images of the at least three channels based on a set frequency;
      an image identifier configured to subject the corresponding images of the at least three channels to target protection component identification and scene analysis, to obtain a relative position relationship of the at least two target protection components; and
      an image pre-processor configured to:
         subject the images of the at least three channels extracted by the image extractor to target object identification, the target object being C-arm X-ray machine system, and
         remove an object other than the identified target object from the images, supply the images from which the object has been removed to a trained image completion model, and obtain completed images outputted by the image completion model, wherein the image identifier is configured to perform the target protection component identification and scene analysis base on the completed corresponding images of the at least three channels; and
   a controller configured to:
      determine whether a possible collision exists based on the relative position relationship of the at least two target protection components; and
      control the C-arm X-ray machine system to stop moving or to slow down a movement by the C-arm X-ray machine system based on the determination of the possible collision.

2. The collision monitoring apparatus as claimed in claim 1, wherein:
   the C-arm X-ray machine system comprises a C-arm X-ray machine and a patient examination platform;
   the at least one target protection component comprises: at least two target protection components, including a bed board of the patient examination platform, and: an X-ray source, an X-ray receiver, and/or a C-arm; and
   the camera includes at least three cameras selected from group of cameras consisting of: one or more cameras located directly above a C-arm X-ray machine of the C-arm X-ray machine system, one or more cameras directly in front of the C-arm X-ray machine, cameras at two sides of the C-arm X-ray machine, and cameras located at two sides of the patient examination platform, the at least three cameras being configured to acquire video images of the surroundings of the at least two target protection components from different directions, respectively, to obtain the video streams of at least three channels.

3. The collision monitoring apparatus as claimed in claim 1, wherein the C-arm X-ray machine system includes a C-arm X-ray machine and a patient examination platform.

4. The collision monitoring apparatus as claimed in claim 1, wherein the at least one target protection component comprises at least two target protection components, including a bed board of the patient examination platform, and at least one of: an X-ray source, an X-ray receiver and a C-arm.

5. The collision monitoring apparatus as claimed in claim 1, wherein the camera comprises at least three cameras selected from group of cameras consisting of: one or more cameras located directly above a C-arm X-ray machine of the C-arm X-ray machine system, one or more cameras directly in front of the C-arm X-ray machine, cameras at two sides of the C-arm X-ray machine, and cameras located at two sides of a patient examination platform of the C-arm X-ray machine, the at least three cameras being configured to acquire video images of the surroundings of the at least one target protection component from different directions, respectively, to obtain the video streams of at least three channels.

6. The collision monitoring apparatus as claimed in claim 1, wherein the camera includes multiple cameras that are configured to collectively acquire at least two video streams of at least two respective channels, the image processor including:
   an image extractor configured to subject the at least two video streams to synchronization, and to extract corresponding images of the at least two channels according to a set frequency; and
   an image identifier configured to subject the extracted corresponding images of the at least two channels, to target protection component identification and scene analysis, to obtain a relative position relationship of the at least one target protection component, wherein
   the controller is configured to determine whether a possible collision exists based on the relative position relationship of the at least one target protection component.

7. The collision monitoring apparatus as claimed in claim 1, wherein:
   the C-arm X-ray machine system includes a position detector configured to determine a current movement position of a C-arm, the at least one target protection component including an X-ray source or an X-ray receiver;
   the camera includes at least one camera mounted at the X-ray source side or at least one camera mounted at the X-ray receiver side;
   the image processor is configured to: determine whether an obstacle appears in a target region according to the video image from the at least one camera, and when an obstacle appears in the target region, determine a current position of the obstacle;
   the controller is further configured to: determine a current movement direction of the C-arm, and in response to the current movement direction is toward the current position of the obstacle: determine a distance value between the target protection component and the obstacle according to the current movement position of the C-arm and the current position of the obstacle, and determine whether a possible collision exists based on the distance value.

8. The collision monitoring apparatus as claimed in claim 7, wherein the movement position comprises: a rotational movement position, an orbital movement position, or a horizontal movement position.

9. The collision monitoring apparatus as claimed in claim 8, wherein the movement direction comprises: a rotational movement forward direction, a rotational movement reverse direction, an orbital movement forward direction, an orbital movement reverse direction, a horizontal movement forward direction, or a horizontal movement reverse direction.

10. A C-arm X-ray machine system comprising the collision monitoring apparatus as claimed in claim 1.

11. A C-arm X-ray machine comprising the collision monitoring apparatus as claimed in claim 1.

12. A collision monitoring method for a C-arm X-ray machine system, the method comprising:
    acquiring a video image of surroundings of at least one target protection component on the C-arm X-ray machine system to obtain video streams of at least three channels;
    determining, by an image processor, a scene of the surroundings of the at least one target protection component based on the video image, the determining the scene including: subjecting the video streams of the at least three channels to synchronization; extracting corresponding images of the at least three channels according to a set frequency; and subjecting the corresponding images of the at least three channels to target protection component identification and scene analysis, to obtain a relative position relationship of the at least two target protection components;
    subjecting, by the image processor, the images of the at least three channels to target object identification, the target object being the C-arm X-ray machine system;
    removing by the image processor, an object other than the identified target object from the current image;
    supplying, by the image processor, the images from which the object has been removed to a trained image completion model;
    obtaining, by the image processor, completed images outputted by the image completion model, wherein subjecting the corresponding images of the at least three channels to target protection component identification and scene analysis includes: performing target protection component identification and scene analysis based on the completed corresponding images of the at least three channels; and
    determining, by a controller, whether a possible collision exists based on the relative position relationship of the at least two target protection components, and control the C-arm X-ray machine system to stop moving or to slow down a movement by the C-arm X-ray machine system based on the determination.

13. The collision monitoring method as claimed in claim 12, wherein:
    the at least one target protection component comprises: at least two target protection components, including a bed board of a patient examination platform, and: an X-ray source, an X-ray receiver, and/or a C-arm; and
    acquiring the video image of surroundings of at least one target protection component on the C-arm X-ray machine system includes acquiring video images of the surroundings of the at least two target protection components from at least three directions, respectively, to obtain the video streams of at least three channels, the at least three directions including at least three of the following directions: directly above, directly in front of, and at two sides of the C-arm X-ray machine, and at two sides of the patient examination platform.

14. The collision monitoring method for a C-arm X-ray machine system as claimed in claim 12, wherein:
    the at least one target protection component comprises: a collimator of the X-ray source or an image enhancer at the X-ray receiver side;
    the acquiring the video image of surroundings of at least one target protection component on the C-arm X-ray machine system includes acquiring a video image of the surroundings of the collimator from the X-ray source side or acquiring a video image of the surroundings of the image enhancer from the X-ray receiver side;
    the determining the scene of the surroundings of the at least one target protection component according to the video image includes determining whether an obstacle appears in the target region according to the video image, and when an obstacle appears in the target region, performing positioning of the obstacle to obtain a current position of the obstacle;
    the method further comprises determining a current movement position and a current movement direction of a C-arm; and
    the determining whether the possible collision exists according to the scene of the surroundings of the at least one target protection component includes: determining whether the current movement direction is toward the current position of the obstacle, and in response to the current movement direction being toward the current position of the obstacle: determining a distance value between the target protection component and the obstacle according to the current movement position of the C-arm and the current position of the obstacle, and determining whether a possible collision exists according to the distance value.

15. A non-transitory computer-readable storage medium with an executable program stored thereon, that when executed, instructs a processor to perform the method of claim 12.

16. A computer program product embodied on a non-transitory computer-readable storage medium and having a computer program which is directly loadable into a memory of the controller of the system, when executed by the controller, causes the system to perform the method as claimed in claim 12.

* * * * *